(12) United States Patent
Lacoste et al.

(10) Patent No.: US 11,123,576 B2
(45) Date of Patent: Sep. 21, 2021

(54) DEVICE FOR TREATMENT OF A TISSUE AND METHOD OF PREPARATION OF AN IMAGE OF AN IMAGE-GUIDED DEVICE FOR TREATMENT OF A TISSUE

(71) Applicant: THERACLION SA, Malakoff (FR)

(72) Inventors: Francois Lacoste, Gentilly (FR); Thierry Pechoux, Paris (FR)

(73) Assignee: THERACLION SA, Malakoff (FR)

( * ) Notice: Subject to any disclaimer, the term of this patent is extended or adjusted under 35 U.S.C. 154(b) by 1009 days.

(21) Appl. No.: 15/106,892

(22) PCT Filed: Dec. 11, 2014

(86) PCT No.: PCT/EP2014/077446
§ 371 (c)(1),
(2) Date: Jun. 21, 2016

(87) PCT Pub. No.: WO2015/096994
PCT Pub. Date: Jul. 2, 2015

(65) Prior Publication Data
US 2017/0001043 A1    Jan. 5, 2017

(30) Foreign Application Priority Data

Dec. 23, 2013 (EP) .................................... 13199292

(51) Int. Cl.
*A61N 7/00* (2006.01)
*A61N 7/02* (2006.01)
(Continued)

(52) U.S. Cl.
CPC ............... *A61N 7/00* (2013.01); *A61B 8/085* (2013.01); *A61B 8/4281* (2013.01);
(Continued)

(58) Field of Classification Search
None
See application file for complete search history.

(56) References Cited

U.S. PATENT DOCUMENTS 7,556,182 B2   7/2009  Murayama et al.
7,753,944 B2   7/2010  Lacoste et al.
(Continued)

FOREIGN PATENT DOCUMENTS

CN    102781516 A    11/2012
CN    103 123 721 A    5/2013
(Continued)

OTHER PUBLICATIONS

International Search Report Corresponding to PCT/EP2014/077446 dated Apr. 20, 2015.
(Continued)

*Primary Examiner* — Yi-Shan Yang
(74) *Attorney, Agent, or Firm* — Finch and Maloney, PLLC; Michael J. Bujold; Jay Franklin

(57) ABSTRACT

A device for treatment of a tissue (8) of a living being, including a transducer (4) for emitting a beam of ultrasound waves mounted on a movable treatment head (1), an ultrasonic imaging device (2, 3), optionally an inflatable balloon (5) surrounding the treatment head (1) and containing a coupling fluid, and a control unit for controlling movement of the treatment head (1) and operation of the transducer (4) and the imaging device (2, 3). In order to avoid displacement of tissues (7, 8) during displacement of the treatment head (1) and increase imaging quality, the treatment head (1) is adjustable to at least two of a treatment position (T), a monitoring position (M) and a travel position (S).

11 Claims, 3 Drawing Sheets

Figure 1:
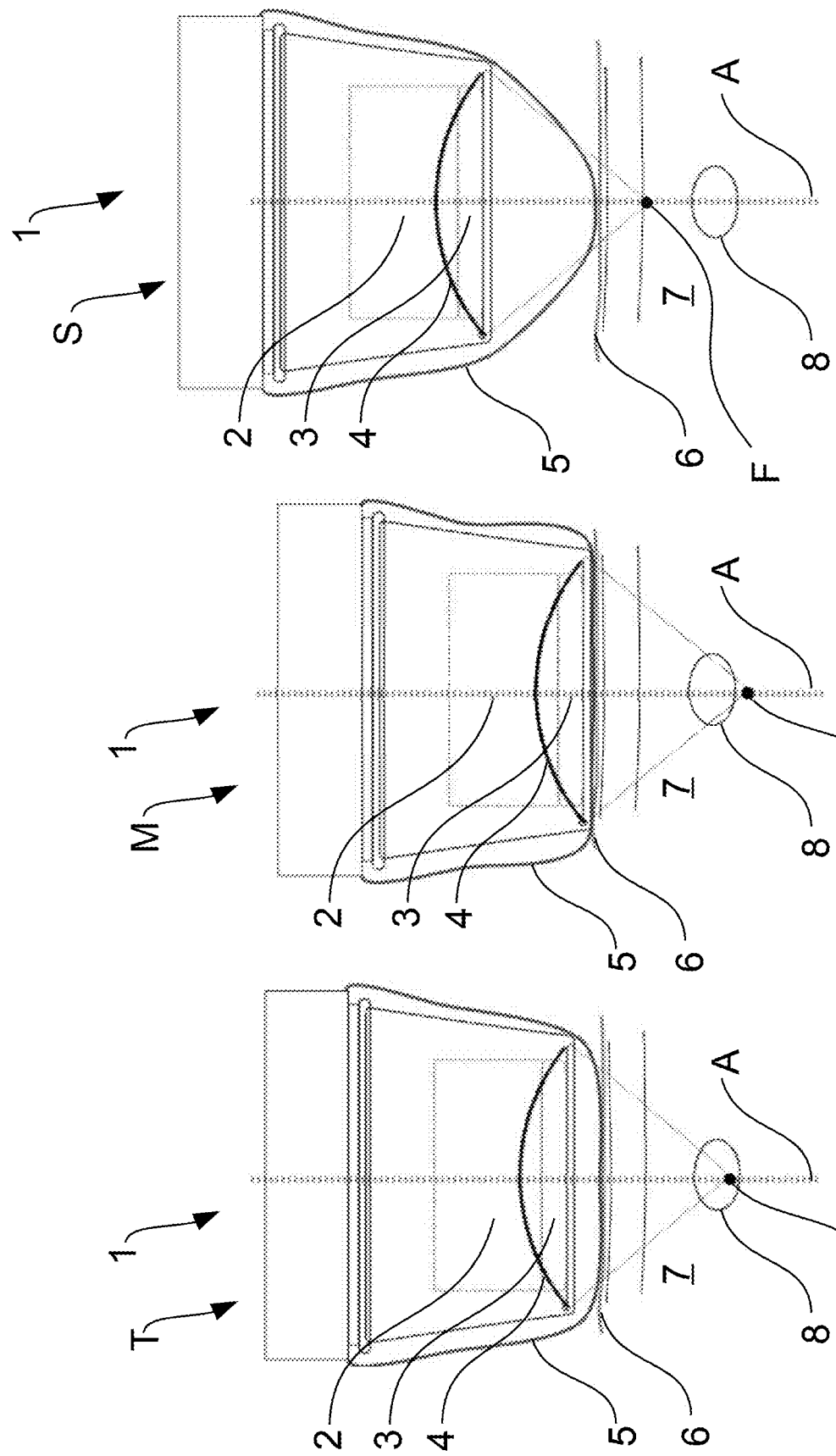

(51) Int. Cl.
*A61B 8/08* (2006.01)
*A61B 8/00* (2006.01)
A61B 34/10 (2016.01)
A61B 90/00 (2016.01)

(52) U.S. Cl.
CPC .............. *A61B 8/4461* (2013.01); *A61B 8/54* (2013.01); *A61N 7/02* (2013.01); *A61B 2034/105* (2016.02); *A61B 2090/378* (2016.02); *A61N 2007/0052* (2013.01); *A61N 2007/0082* (2013.01)

(56) References Cited

U.S. PATENT DOCUMENTS

| | | | |
|---|---|---|---|
| 9,033,886 B2 | 5/2015 | Lacoste et al. | |
| 2002/0198470 A1* | 12/2002 | Imran | A61B 5/0538 600/587 |
| 2004/0254620 A1* | 12/2004 | Lacoste | A61N 7/02 607/96 |
| 2011/0112405 A1* | 5/2011 | Barthe | A45D 44/005 600/459 |
| 2012/0172710 A1* | 7/2012 | Anthony | A61B 5/6843 600/411 |
| 2013/0046209 A1* | 2/2013 | Slayton | A61N 7/02 601/3 |
| 2014/0213903 A1* | 7/2014 | Seo | A61B 8/085 600/439 |

FOREIGN PATENT DOCUMENTS

| | | | | |
|---|---|---|---|---|
| CN | 103123721 A | * | 5/2013 | |
| EP | 2 327 450 A1 | | 6/2011 | |
| EP | 2 332 614 A1 | | 6/2011 | |
| WO | 2006/120947 A1 | | 11/2006 | |
| WO | 2009/149390 A1 | | 12/2009 | |
| WO | WO-2011064209 A1 | * | 6/2011 | .............. A61B 50/00 |

OTHER PUBLICATIONS

Written Opinion Corresponding to PCT/EP2014/077446 dated Apr. 20, 2015.
Chinese Office Action issued in corresponding Chinese Patent Application No. 201480066612.9 dated May 28, 2018.

* cited by examiner

DEVICE FOR TREATMENT OF A TISSUE AND METHOD OF PREPARATION OF AN IMAGE OF AN IMAGE-GUIDED DEVICE FOR TREATMENT OF A TISSUE

The invention relates to a device for treatment of a tissue of a living being and a method for preparation of an image according to the independent patent claims.

The device includes a transducer for emitting a beam of ultrasound waves, preferably high intensity focused ultrasound waves for irradiating the tissue. The transducer is mounted on a movable treatment head. The beam is focused on or focusable onto a focal point. An ultrasonic imaging device is mounted on the treatment head and has an imaging plane intersecting the focal point. Optionally, an inflatable balloon surrounding at least partially the treatment head, containing a coupling fluid and defining a contact surface of the treatment head may be provided. A control unit is used for controlling the movement of the treatment head and the operation of the transducer and the imaging device.

Ultrasound waves, in particular high intensity focused ultrasound (HIFU) are mainly used for treatment of tumours of breast, thyroid, prostate and uterus. High intensity ultrasound waves are focused onto a focal point located within the tumour to be treated. During irradiation, heat is created when the acoustic waves are absorbed by the tissue. The temperature can rise up to 85° C., whereby the tissue is destroyed by coagulation necrosis. One big advantage of a treatment with HIFU is that it is noninvasive, thereby considerably reducing risks for the patient.

In order to treat large tumours, the focal point is moved along the tissue (scanning). Scanning can occur by moving the treatment head, known as mechanical scanning, or by keeping the treatment head fixed and move the focal point using phase array technique, known as electronic scanning. Due to its simplicity and low cost, mechanical scanning is preferred.

Because a treatment with HIFU also provides some energy in the tissue located adjacent to the focal point, therefore possibly damaging also those tissues, it is common to operate a device for treatment in a way known as "pulse and pause method" wherein an irradiation period is followed by a pause period without irradiation, in order allow the tissue region to cool down.

The pause period is usually used to proceed with auxiliary tasks such as verification of the position of the focal point with respect to the target using the imaging device or movement of the treatment head to the next location in a scanning pattern.

In order to cool the tissues located before the focus, a balloon containing a coupling fluid and arranged between transducer and tissue to be treated may be used. Such a device is shown as an example in WO 2006/120947.

When using such a device, the problem arises that a motion of the treatment head might displace the tissue of a patient, e.g. because of friction between the tissue and the balloon surface. Further, motion of the treatment head may be impaired by mechanical interferences between the treatment head and the tissue of a patient, e.g. by friction or lack of clearance between the tissue and the balloon surface. There is therefore the risk that because of the tissue displacement, certain areas of the tissue to be treated may be over- or undertreated.

To control the treatment, monitoring of the focal point and of the tissue to be treated using real-time imaging such as echography, magnetic resonance imaging or fluoroscopy is used. Image quality may, however, be poor, in particular when using echography as a real-time image source, because of the large distance between the imaging device and the tissue and because of interferences between the ultrasound beam of the transducer and the ultrasound beam of the imaging device.

It is therefore an object of the present invention to solve the problems of the prior art and in particular to provide a device which can reliably allow mechanical scanning of a tissue to be treated and at the same time provide high quality images of the tissue to be treated.

This problem is solved with a device according to the claim 1 and with a method according to the claim 11 of the present invention.

The device includes a transducer for emitting a beam of ultrasound waves, preferably high intensity focused ultrasound waves, for irradiating the tissue. The transducer is mounted on a movable treatment head. The beam is focused on or focusable onto a focal point. An ultrasonic imaging device is mounted on the treatment head and has an imaging plane intersecting the focal point. Optionally, an inflatable balloon surrounding at least partially the treatment head, containing a coupling fluid and defining a contact surface of the treatment head may be provided. A control unit is provided for controlling the movement and/or position of the treatment head and the operation of the transducer and the imaging device.

The treatment head is adjustable along an axis (A) to at least two of a treatment position, a monitoring position and a travel position. In the monitoring position the distance between the transducer and the tissue is smaller than in the treatment position. In the travel position a distance between the contact surface and the tissue or between the transducer and the tissue is larger than in the treatment position or the compression force onto the tissue is reduced.

The control unit is further adapted to trigger the transducer to emit ultrasound waves when the treatment head is in the treatment position, to position the treatment head along a plane substantially perpendicular to the axis (A) when the treatment head is in the travel position, and perform imaging of an area surrounding the tissue at least when the treatment head is in the monitoring position.

The treatment head is displaced along a scanning pattern along a plane substantially perpendicular to the axis (A) preferably only when it is in the travel position, in order to reduce friction between a contact surface and the tissue and therefore avoid displacement of the tissue. In order to improve the image quality, imaging is preferably performed only with the treatment head in the monitoring position, where a distance between the transducer, and thus between the imaging device, is smaller than in the treatment position. This is in particular advantageous when the device is also adapted to perform elastography. The control unit is adapted to allow the respective operations only when the treatment head is in the appropriate position as shown above.

This movement of the treatment head is particularly advantageous in order to reduce or displace appearance of skin artefacts, also known as "skin ghost". A skin ghost appears when the tissue boundary layer, depending from the tissue e.g. a skin or a mucosa, reflects the imaging beam back to the imaging device, which is successively reflected back to the skin or mucosa and then back to the imaging device again. The skin ghost appears in the image as a bright line located within the tissue at approximately twice the distance between the skin or mucosa and the beginning of the image, which may correspond to the surface of the imaging device or not. The skin ghost is particularly unwanted when it is located within the target area, that means within the tissue to be treated.

In the treatment position, the focal point is located on the desired spot of tissue to be treated within the target area.

In absence of an inflatable balloon, the contact surface with the skin is defined by an ultrasonic imaging device head or by the transducer surface. The control unit according to the present invention may be therefore used also in devices not having such a balloon. Alternatively, the balloon may be of a fixed shape, e.g. a bell-shaped cover element, and arranged movable with respect to the treatment head.

Imaging of the tissue may be performed in every position and also in positions located between the defined positions.

Preferably, the contact between the contact surface and the tissue is maintained when the treatment head is in the travel position, in order to allow continuous imaging and maintain cooling of the tissue. In this case, only the compression force is reduced.

The control unit is preferably adapted to move the treatment head from the travel position to the treatment position before an ultrasound pulse is emitted from the transducer. Accordingly, the treatment head is first positioned on a spot along a scanning pattern and then lowered to the treatment position, where the transducer is triggered to emit an ultrasound pulse of given power and duration.

The control unit is further preferably adapted to move the treatment head from the travel position to the monitoring position to monitor the tissue by means of the imaging device and then to the treatment position before an ultrasound pulse is emitted from the transducer. After positioning of the treatment head as described above, the treatment head is lowered first to the monitoring position in order to improve imaging, where the tissue is monitored. The position of the treatment head can therefore be controlled and an eventually occurred displacement of tissue can be recognized. Controlling the position can occur either manually by an operator by means of a display and other adequate means or automatically, by implementing an automatic recognition of displacement of the tissue in the control device or another adequate means. If the tissue is positioned correctly, the treatment head is then raised to the treatment position, where treatment of the tissue takes place. If a displacement of the tissue is recognized, a new positioning of the treatment head may be triggered, whereby the treatment head is moved to the travel position.

Preferably, the control unit is adapted to move the treatment head, after emission of an ultrasound pulse from the transducer, from the treatment position to the monitoring position, in order to monitor the effect of the delivered ultrasound waves.

The control unit is further preferably adapted to then move the treatment head to the treatment position for further emission of an ultrasound pulse from the transducer, in particular if, when monitoring the effect of the delivered ultrasound pulse, it is recognized that the effect of the delivered ultrasound waves did not achieve a desired level.

Preferably, the control unit is adapted to move the treatment head to the travel position for further positioning of the treatment head once achievement of a desired level of treatment has been recognized. When proceeding with scanning the tissue, the treatment head is moved along a scanning path. In order to avoid displacement of the tissue, the treatment head is preferably displaced only when in the travel position.

Further preferred, the control unit is adapted to control the position and or adjustment of the treatment head using the ultrasonic imaging device. Preferably, adjustment of the treatment head along the axis (A) is controlled by means of the ultrasonic imaging device. When using the ultrasonic imaging device, the distance between the treatment head and the tissue can be easily monitored, in particular by detecting the interface of the tissue contacting the contact surface of the balloon, which thanks to the coupling fluid which has a low absorption of ultrasound, is clearly seen on a display by a user (normally as a white stripe) or can be detected automatically by the control unit or other adequate means. The control unit is preferably also adapted to control the position of the treatment head in a plane substantially perpendicular to the axis (A).

The control unit is preferably adapted to control the pressure in the balloon. Therefore, the device is equipped with a fluid system coupled to the balloon for handling the coupling fluid, preferably including at least one pump for filling and/or emptying the balloon. Further, a pressure sensor may be present in the balloon in order to control the pressure in the balloon, the pressure sensor and the at least one pump preferably being connected to the control unit or other adequate means for regulating the pressure in the balloon. The volume of the coupling fluid may also be controlled and regulated by known means.

Pressure control is particularly advantageous to adjust the pressure in the balloon to an optimal value, in particular for each of the treatment position, the monitoring position and the travel position.

Further preferred, the control unit is adapted to bring the pressure in the balloon to a first value when the treatment head is in the travel position and to a second value higher than the first value when the treatment head is in the treatment position and/or in the monitoring position. Accordingly, by reducing the pressure when the treatment head is in the travel position, friction between tissue and balloon can be reduced, with the known advantages. Further, by increasing the pressure when the treatment head is in the treatment position and/or in the monitoring position, the compression reduces blood flow in the tissue, thereby reducing also heat dissipation. In other words, an higher temperature in the focal point may be achieved with the same beam power.

Alternatively, the treatment head as such may remain in the same position in the treatment position and travel position. In order to improve imaging and fix the tissue, the pressure in the balloon is then raised when the treatment head is in the treatment position. The pressure may be additionally raised/lowered accordingly when the treatment head is in the imaging position. This is particularly advantageous when reducing and or/displacing the appearance of a skin ghost.

The invention also relates to a method for operating a device for treatment of a tissue of a living being. Preferably, the device is a device as described above. Reference to the advantages and alternatives cited above is therefore made.

The invention further relates to a method of preparation of an image of an image-guided therapeutic device. The device includes a treatment head with a transducer for emitting a beam of ultrasound waves, preferably high intensity focused ultrasound waves, for irradiating a tissue. The beam is focused on or focusable onto a focal point. The device further includes an ultrasonic imaging device having an imaging plane which optionally may intersect the focal point. The invention further relates to a device adapted to perform preparation of an image.

As cited above, the appearance of a skin ghost is disadvantageous, in particular when located within the target area.

It is therefore a further object of the present invention to provide a method and a device which can reliably provide identification of an artefact known as skin ghost and therefore simplify visualisation and recognition of the target area by a user person or automatically by a control device or other adequate means.

The method of preparation of an image according to the present invention is performed with a device including a treatment head with a transducer for emitting a beam of ultrasound waves, preferably high intensity focused ultrasound waves, for irradiating a tissue. The beam is focused on or focusable onto a focal point. The device further includes an ultrasonic imaging device having an imaging plane which optionally may intersect the focal point.

Preferably, the device comprises also an inflatable balloon surrounding at least partially the treatment head and containing a coupling fluid. Further preferred, the device is a device as described above.

According to the method, an image of a treatment region is provided and is displayed on a display.

Successively, a width sector ($x_{min}$, $x_{max}$) of the treatment region to be analyzed is chosen. This can be done either manually by a user person selecting with adequate means such as a user interface comprising a mouse, a tracking ball or the like the width sector to be analyzed or automatically by a control device or by other adequate means. Alternatively, an area of the image to be analyzed may be chosen by dragging a cursor (or a finger if using a touch screen) over it.

A line representing an artefact, preferably a skin ghost, is then drawn and is visualized on the display together with the image of the treatment region. In other words, a virtual line representing the run of the skin ghost or approximating the run of the skin ghost is visualized on the image of the treatment region. The line representing the artefact may not overlap the artefact but may be displayed displaced with respect to the artefact itself, in order to simplify recognition of the artefact by an user person (or automatically). Instead of a line, other suitable graphical means such as dots, highlighting, etc. may be used.

The line representing the artefact is preferably drawn by determining the skin surface line in the chosen width sector. Determining the skin surface line (which could also be a mucosa surface line) is done either manually by a user person as described above, or automatically by recognizing the first ultrasound wave reflection surface in the chosen width sector by known techniques.

The distance between the skin surface line and the beginning of the image corresponding to the ultrasonic imaging device ($y_n$) for every width point ($x_n$) within the chosen width sector ($x_{min}$, $x_{max}$) is then determined. The beginning of the image according to the present invention is meant to be the end of the image which corresponds to the location of the imaging device, thus being located in the ultrasound wave propagation direction upstream with respect to the skin surface.

Optionally, after determining an offset value (A) of the image corresponding to an offset of the beginning of the image, a line ($y_s$) at a distance twice the distance between the skin surface line and the beginning of the image corresponding to the ultrasonic imaging device ($y_n$) plus an optional offset value (A) thus fulfilling the equation $y_s=2*y_n$ (+A), is drawn from the beginning of the image corresponding to the ultrasonic imaging device. Therefore, the location of the skin ghost can be easily seen by a user person or, if being determined automatically, can be taken into consideration when further analyzing the image, in particular when relevant factors related to the target area such as size, volume, tissue characteristics are being determined.

Preferably, the offset value (A) is a characteristic of the imaging device and must therefore not be determined every time when performing the method according to the present invention.

Preferably, as cited above, determining the width sector ($x_{min}$, $x_{max}$) of the treatment region to be analyzed and/or the skin surface line is performed automatically by an image analysis program.

The invention also solves the known problem with a device including a calculating unit adapted to perform the following steps: providing an image of a treatment region; displaying the image on a display; choosing a width sector ($x_{mix}$, $x_{max}$) of the treatment region to be analyzed; drawing a line representing an artefact, preferably a skin ghost, and visualizing the line on the display together with the image of the treatment region.

The device may be integral part of a device for treatment of a tissue or may be a separate device, which is however at least connected with an imaging output of the device for treatment.

Drawing a line representing an artefact is preferably done by determining a skin surface line in the chosen width sector; determining the distance between the skin surface line and the beginning of the image corresponding to the ultrasonic imaging device ($y_n$) for every width point ($x_n$) within the chosen width sector ($x_{min}$, $x_{max}$); optionally, determining an offset value (A) of the image; drawing a line ($y_s$) at a distance=$2*y_n$+A from the beginning of the image corresponding to the ultrasonic imaging device.

The device according to the present invention is able to perform in particular a method according to the present invention. The advantages of the method according to the present invention therefore apply also to the device according to the present invention.

Figure 2:
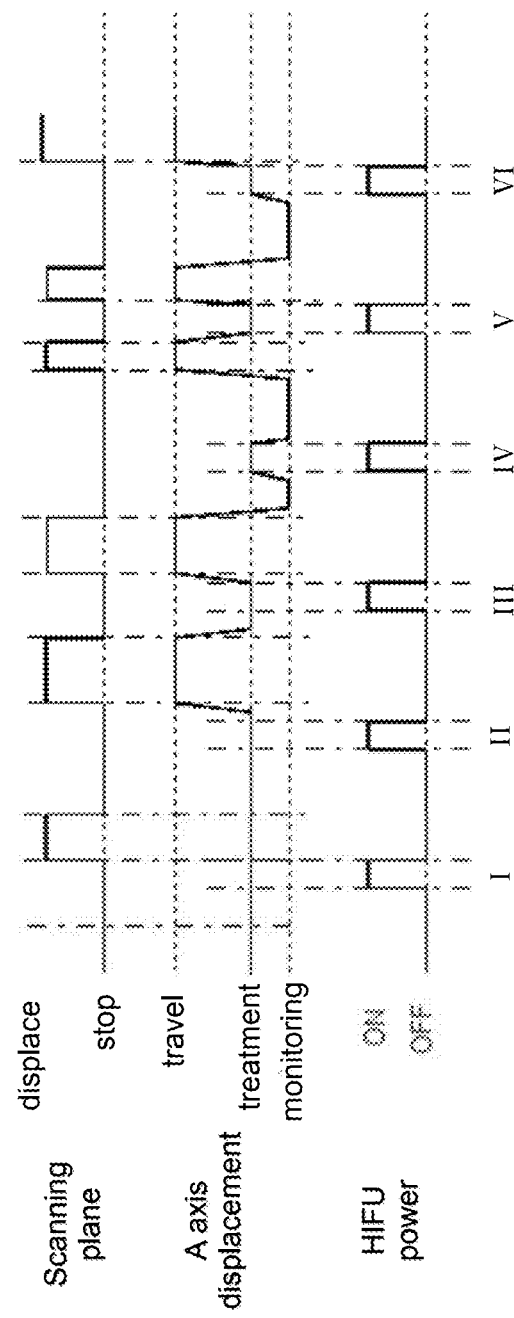
Figure 3:
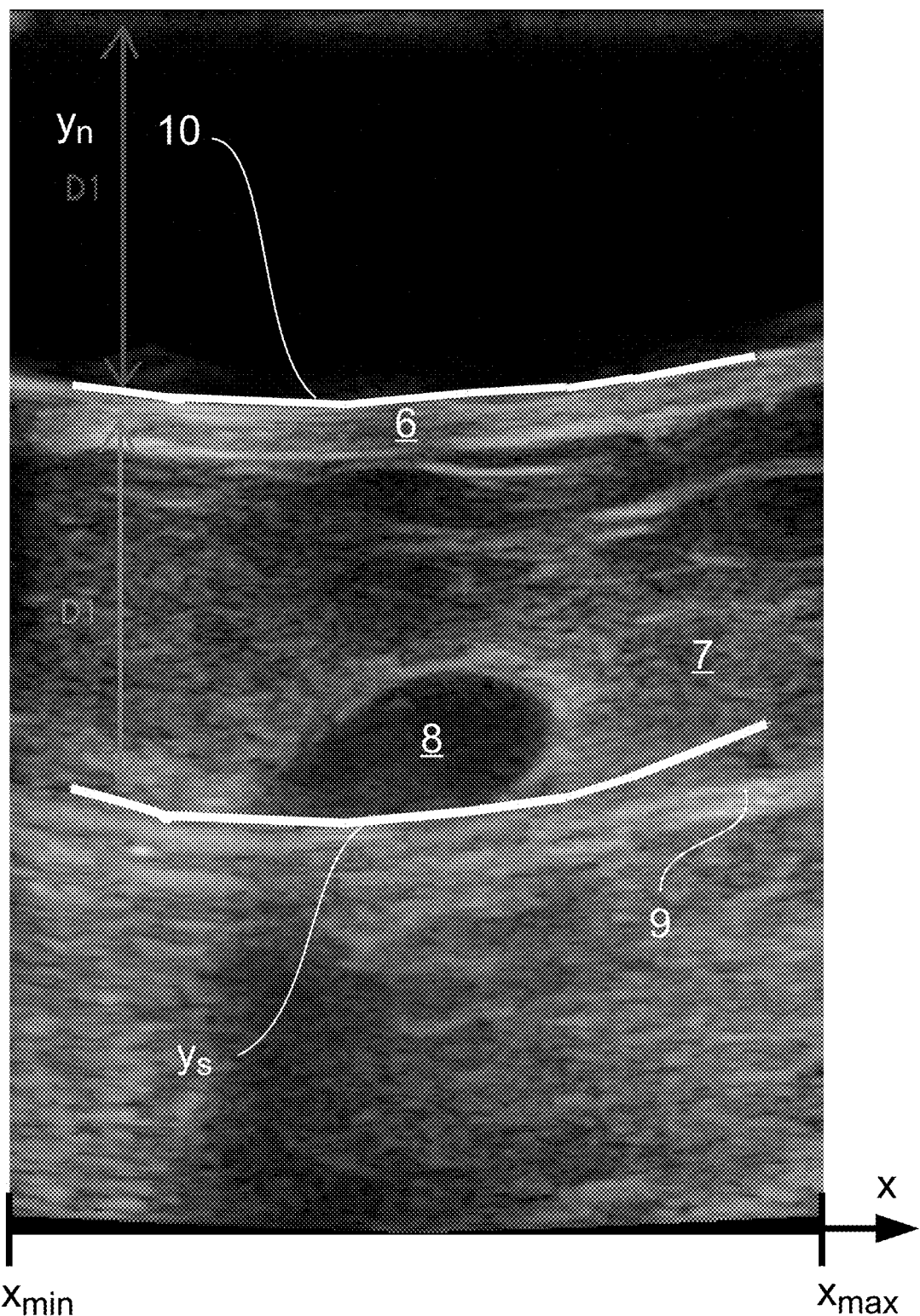

The invention will be described below by means of a preferred embodiment in connection with the figures. The figures show:

FIG. 1: a schematic sectional view of a device according to the present invention in, from left to right, a treatment position, monitoring position and travel position;

FIG. 2: a schematic view of a displacement pattern of the treatment head according to the method of the present invention;

FIG. 3: a view of a displayed image, where a skin ghost has been identified with a method according to the present invention.

FIG. 1 shows a treatment head 1 in a sectional view, whereby the section plane corresponds to an imaging plane of an echography device 2. An imaging array 3 of the echography device is arranged within an HIFU transducer 4 having a shape of a section of a sphere surface. The transducer 4 is of a fixed-focal-point type, the beam of ultrasound waves emitted by the transducer 4 being focused on a focal point F.

The transducer is enclosed by a flexible membrane 5 of a material with low ultrasound reflection and is filled with an ultrasound coupling fluid.

The membrane 5 is contacting a skin 6 of a patient delimiting a tissue 7 and thus defining a contact surface. A tumour 8, which must be treated, is located within the tissue 7.

The treatment head 1 is shown in the FIG. 1 in three different positions, namely from left to right a treatment position T, a monitoring position M and a travel position S.

Movement of the treatment head 1, emission of the HIFU beam by the transducer 4 and imaging of the tissue 7 and if need be of the tumour 8 as well as other functions are controlled by a control unit (not shown), which may be performed fully automatically, semi-automatically or manually, meaning that each step must be confirmed by an user person, or a combination thereof.

In the treatment position T, the focal point F of the HIFU beam is focused on the tumour 8, in order to treat the tumour 8.

In the monitoring position M, the treatment head 1 is lowered along an axis A with respect to the skin 6 compared to the treatment position T such that the distance between the imaging array 3 of the echography device 2 is as small as possible, thus increasing the image quality and reducing the appearance of skin artefacts known as skin ghost. The HIFU beam is not focused on the tumour 8.

In the travel position S, the treatment head 1 is raised along an axis A with respect to the skin 6 compared to the treatment position, whereby a contact between the membrane 5 and the skin 6 is kept in order to ensure coupling of the echography device 2 and cooling of the skin 6 and tissue 7. The HIFU beam is also not focused on the tumour 8. As an alternative, the pressure in the membrane may be adjusted in order to reduce friction, while keeping the treatment head 1 in a constant position. In another alternative, the membrane 5 or other equivalent means may be displaced with respect to the treatment head 1, which is kept in the same position. Combination of those alternatives may also be possible.

In FIG. 2, different displacing patterns of the treatment head 1 are schematically shown. The upper line indicates if the treatment head 1 is moving along a scanning pattern ("displace") or is at rest ("stop"). The line in the middle indicates the position of the treatment head 1 along the axis A. The bottom line shows if the HIFU transducer 4 is operated ("ON") or not ("OFF").

The HIFU transducer 4 is located at a first treatment point I and is triggered to emit an HIFU beam and is successively moved along the scanning pattern in a plane substantially perpendicular to the axis A, referred to in FIG. 2 as the "scanning plane", to reach the next treatment point II. During displacement from the treatment point I to the treatment point II, no displacement of the treatment head 1 along the axis A takes place. The treatment head 1 is kept in the treatment position T, as known from the prior art.

According to the present invention, before the treatment head 1 is displaced from the treatment point II to the treatment point III, the treatment head 1 is moved from the treatment position T to the travel position S along the axis A, then displaced along the scanning plane and subsequently moved back to the treatment position T, where a HIFU beam is emitted.

The treatment head 1 is then moved again from the treatment position T to the travel position S along the axis A and then displaced in the scanning plane from the treatment point III to the treatment point IV. The treatment head 1 is then moved from the travel position S to the monitoring position M along the axis A, where imaging of the tissue 7 and of the tumour 8 takes place, and further to the treatment position T along the axis A, where a HIFU beam is emitted. After emission of the HIFU beam, the treatment head 1 is moved again to the monitoring position M along the axis A for imaging the tissue 7 and tumour 8 and check the effect of the emitted HIFU beam.

The treatment head 1 is further moved to the travel position S along the axis A and displaced to the next treatment point V, where it is moved back along the axis A to the treatment position T and a HIFU beam is delivered.

When displacing the treatment head 1 from the treatment point V to the treatment point VI, the treatment head 1 is moved along the axis A from the treatment position T to the travel position S and then displaced in the scanning plane. The treatment head 1 is then moved to the monitoring position M along the axis A to perform imaging of the tissue 7 and tumour 8 and then to the treatment position T where a HIFU beam is emitted.

FIG. 3 shows an image treated with a method according to the present invention is shown.

The beginning of the image corresponding to the echography device 2 is the upper edge of the image. The width of the analyzed sector ranges from $x_{min}$ to $x_{max}$.

The skin 6 is displayed as a thick bright curved line, the tumour 8 as a black surface about in the middle of the image. In the upper part of the image between the beginning of the image and the skin 6, the coupling fluid is displayed as a dark surface.

In the lower part of the tumour 8, a second bright curved line 9 running parallel to the skin 6 is displayed. This curved line is referred to as a skin ghost and covers a sector of the tumour 8, thus impeding correct imaging of the tissue 7.

After determination of the region corresponding to a run of the skin 6, which is done either manually or automatically by known techniques and is shown schematically by a curve 10, a distance $y_n$ between the beginning of the image and the line 10 is determined over the whole width of sector (from $x_{min}$ to $x_{max}$). Then, a second line $y_s$ representing the skin ghost 9 is drawn at twice the distance $y_n$ from the beginning of the image. In FIG. 3, an offset A is set to zero.

This helps in improving recognition of the skin ghost 9. In case the skin ghost 9 overlaps the tumour 8, the treatment head 1 may be moved along the axis A in order to shift the skin ghost 9 downward and allow imaging of the whole tumour 8.

The invention claimed is:

1. A device for treatment of a tissue of a living being, the device comprising:
   a transducer configured for emitting at least one beam of ultrasound waves for irradiating the tissue, the transducer being mounted on a treatment head, said treatment head being movable, having at least a treatment position, a travel position, and a monitoring position and the beam being focused on or focusable onto a focal point;
   an ultrasonic imaging device mounted on the treatment head and having an imaging plane intersecting the focal point; and
   the treatment head displaceable in a scanning plane substantially perpendicular to a vertical axis only when the treatment head is in the travel position,
   the transducer being adapted to be triggered to emit the at least one beam of ultrasound waves only when the treatment head is in the treatment position, and
   the imaging device being adapted to perform imaging of an area surrounding the tissue at least when the treatment head is in the monitoring position;
   wherein the treatment head is adjustable, by raising and lowering along the vertical axis, to at least the treatment position, the monitoring position and the travel position,
   in the monitoring position, a vertical distance between the transducer and the tissue is shorter than the vertical distance between the transducer and the tissue in the treatment position, and in the travel position, compared to the treatment position, the treatment head is displaced vertically such that a vertical distance between a contact surface of the treatment head and the tissue is longer, or the vertical distance between the transducer and the tissue is longer, or a compression force onto the tissue is reduced.

2. The device according to claim 1, wherein the treatment head is adapted to be moved automatically from the travel position to the treatment position before the at least one ultrasound wave is emitted from the transducer.

3. The device according claim 2, wherein the treatment head is adapted to be moved automatically, after the emission of the at least one ultrasound wave from the transducer, from the treatment position to the monitoring position.

4. The device according to claim 3, wherein the treatment head is adapted to be moved automatically to the treatment position for further emission of an ultrasound pulse from the transducer after the treatment head is brought from the treatment position to the monitoring position.

5. The device according to claim 2, wherein the treatment head is adapted to be moved automatically to the travel position for further positioning of the treatment head after a preceding movement.

6. The device according to claim 1, wherein the treatment head is adapted to be moved automatically from the travel position to the monitoring position to monitor the tissue via the imaging device and then to the treatment position before the at least one ultrasound wave is emitted from the transducer.

7. The device according claim 6, wherein the treatment head is adapted to be moved automatically, after the emission of an ultrasound wave from the transducer, from the treatment position to the monitoring position.

8. The device according to claim 7, wherein the treatment head is adapted to be moved automatically to the treatment position for further emission of an ultrasound pulse from the transducer after the treatment head is brought from the treatment position to the monitoring position.

9. The device according to claim 1, wherein at least one of a position of the treatment head, and an adjustment of the treatment head, is based on a distance between the treatment head and the tissue.

10. A device according to claim 1, further comprising an inflatable balloon, wherein the inflatable balloon at least partially surrounds the treatment head, contains a coupling fluid, and defines a contact surface of the treatment head.

11. A method of operating a device for treatment of a tissue of a living being, the device comprising:
   a transducer configured for emitting a beam of ultrasound waves for irradiating the tissue, the transducer being mounted on a treatment head, said treatment head being movable, having at least a treatment position, a travel position, and a monitoring position, and the beam being focused on or focusable onto a focal point; and
   an ultrasonic imaging device, mounted on the treatment head, and having an imaging plane intersecting the focal point;
   in the monitoring position, a vertical distance between the transducer and the tissue is shorter than the vertical distance between the transducer and the tissue in the treatment position,
   in the travel position, compared to the treatment position, the treatment head moves vertically such that a vertical distance between a contact surface of the treatment head and the tissue is longer, or a distance between the transducer and the tissue is longer, or the compression force on the tissue is reduced the method comprising:
   adjusting the treatment head by raising or lowering along a vertical axis to the treatment position, the monitoring position, and the travel position,
   triggering the transducer to emit at least one beam of ultrasound waves only when the treatment head is in the treatment position,
   displacing the treatment head in the scanning plane substantially perpendicular to the vertical axis only when the treatment head is in the travel position, and
   performing imaging of an area surrounding the tissue at least when the treatment head is in the monitoring position.

* * * * *